(12) United States Patent
Nocker et al.

(10) Patent No.: US 11,376,265 B2
(45) Date of Patent: Jul. 5, 2022

(54) TREATMENT OF MODERATE TO SEVERE INFLUENZA

(71) Applicant: ASPIAIR GMBH, Gemünden (DE)

(72) Inventors: Karlheinz Nocker, Reiskirchen (DE); Sebastian Canisius, Ebsdorfergrund (DE); Gerhard Scheuch, Wohratal (DE)

(73) Assignee: ASPIAIR GMBH, Gemünden (DE)

( * ) Notice: Subject to any disclaimer, the term of this patent is extended or adjusted under 35 U.S.C. 154(b) by 11 days.

(21) Appl. No.: 16/065,600

(22) PCT Filed: Dec. 22, 2016

(86) PCT No.: PCT/EP2016/082307
§ 371 (c)(1),
(2) Date: Jun. 22, 2018

(87) PCT Pub. No.: WO2017/109037
PCT Pub. Date: Jun. 29, 2017

(65) Prior Publication Data
US 2019/0134066 A1 May 9, 2019

(30) Foreign Application Priority Data
Dec. 22, 2015 (EP) ..................................... 15202212

(51) Int. Cl.
| | | |
|---|---|---|
| *A61K 31/616* | (2006.01) | |
| *A61K 9/08* | (2006.01) | |
| *A61K 31/167* | (2006.01) | |
| *A61K 31/215* | (2006.01) | |
| *A61K 9/00* | (2006.01) | |
| *A61K 45/06* | (2006.01) | |
| *A61P 31/16* | (2006.01) | |

(52) U.S. Cl.
CPC .......... *A61K 31/616* (2013.01); *A61K 9/0078* (2013.01); *A61K 9/08* (2013.01); *A61K 31/167* (2013.01); *A61K 31/215* (2013.01); *A61K 45/06* (2013.01); *A61P 31/16* (2018.01)

(58) Field of Classification Search
CPC .............. A61K 2300/00; A61K 31/167; A61K 31/215; A61K 31/616; A61K 45/06; A61K 9/0078; A61K 9/08; A61P 31/16
USPC ........................................................ 514/159
See application file for complete search history.

(56) References Cited

U.S. PATENT DOCUMENTS

| | | | | |
|---|---|---|---|---|
| 6,401,710 B1 * | 6/2002 | Scheuch | ........... | A61M 15/0086 128/200.21 |
| 6,681,762 B1 * | 1/2004 | Scheuch | ............... | A61M 15/00 128/200.14 |
| 8,668,901 B2 * | 3/2014 | Muellinger | ............ | A61K 31/58 424/43 |
| 10,149,823 B2 * | 12/2018 | Yadidi | ............... | A61M 15/0045 |
| 10,195,147 B1 * | 2/2019 | Yadidi | ............... | A61M 15/0086 |
| 2006/0247161 A1 * | 11/2006 | Planz | ..................... | A61K 31/00 514/569 |
| 2009/0191207 A1 * | 7/2009 | Planz | ..................... | A61K 31/00 424/139.1 |
| 2012/0017892 A1 * | 1/2012 | Ludwig | .................. | A61K 9/008 128/200.14 |

FOREIGN PATENT DOCUMENTS

| | | |
|---|---|---|
| WO | WO 2004/060360 | 7/2004 |
| WO | WO 2009/089822 | 7/2009 |

OTHER PUBLICATIONS

Clinical Trials Register—EudraCT No. 2012-004072-19, EU Clinical Trials Register European Union, accessed on Sep. 10, 2018 (https://www.clinicaltrialsregister.eu/ctr-search/trial/2012-004072-19/DE ), 2012).
International Search Report of International Application No. PCT/EP2016/082307, dated Feb. 3, 2017, 3 pages.
Mazur et al., "Acetylsalicylic acid (ASA) blocks influenza virus propagation via its NF-kB-inhibiting activity", Cellular Microbiology, vol. 9(7), p. 1683-1694, (2007).
Scholtissek et al., "Failure to obtain drug-resistant variants of influenza virus after treatment with inhibiting doses of 3-deazaadenosine and H 7", Arch Virol., vol. 119, p. 111-118, (1991).
Rayner et al., "Pharmacokinetic-Pharmacodynamic Determinants of Oseltamivir Efficacy Using Data from Phase 2 Inoculation Studies," Antimicrobial Agents and Chemotherapy, vol. 57, No. 8, pp. 3478-3487, (2013).
Recommendation of the Japanese Society of Infectious Diseases "Indications for the use of anti-influenza drugs (revised edition)", 2011, the Japanese Society of Infectious Diseases, New Influenza Countermeasures Committee, p. 1-11<URL=http://www.kansensho.or.jp/modules/guidelines/index.php?content_id=25>.

* cited by examiner

*Primary Examiner* — Heidi Reese

(74) *Attorney, Agent, or Firm* — Hoxie & Associates LLC

(57) ABSTRACT

The invention provides a compound, namely acetylsalicylic acid (ASA) or a pharmaceutically acceptable salt thereof or a pharmaceutical composition comprising ASA or a pharmaceutically acceptable salt thereof, for use in the treatment of a patient, e.g. a human being, suffering from a severe influenza virus infection and/or a symptom or condition associated therewith (namely, nasal congestion, sore throat, cough, fever, fatigue, headache and myalgias), wherein said use comprises the administration of a composition comprising ASA or a pharmaceutically acceptable salt thereof to the patient by inhalation.

15 Claims, 4 Drawing Sheets

Figure 2:
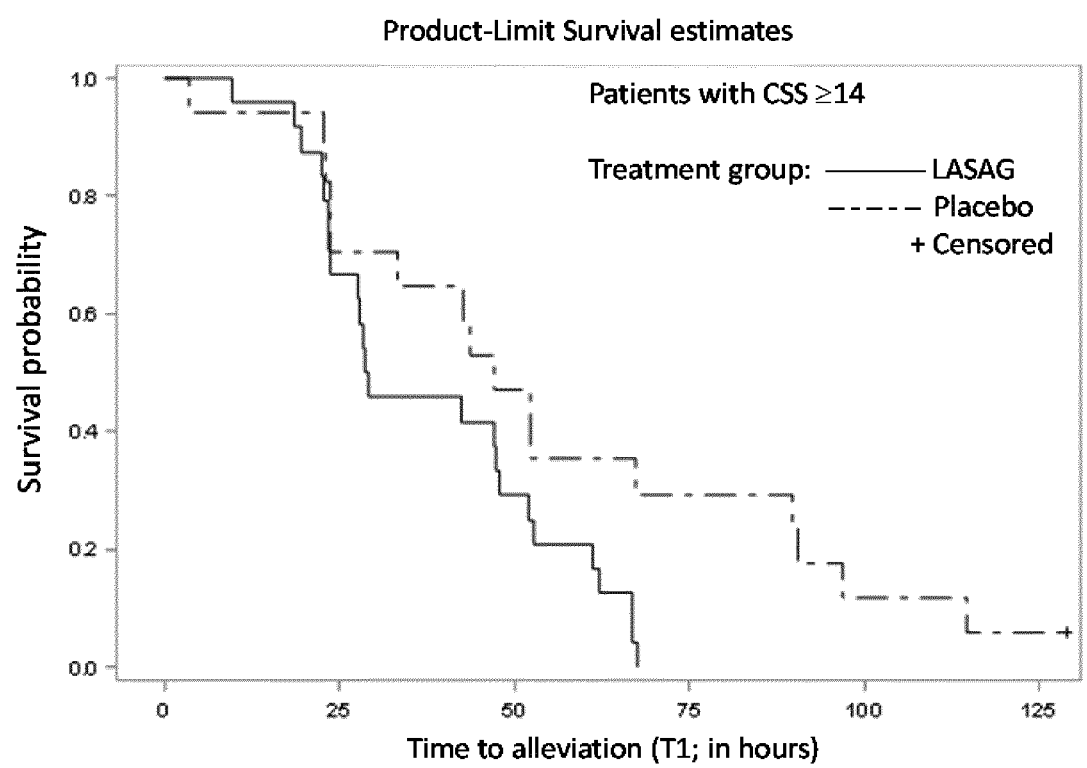

| Please tick the boxes below describing the best to which extent the inluenza symptom appears: | | | | |
|---|---|---|---|---|
| | Not present (like before the influenza) | Mild Form | Moderate Form | Severe Form |
| Stuffed nose | 0 | 1 | 2 | 3 |
| Sore throat | 0 | 1 | 2 | 3 |
| Cough | 0 | 1 | 2 | 3 |
| Muscle pain / Pain in the limbs | 0 | 1 | 2 | 3 |
| Fatigue / Exhaustion | 0 | 1 | 2 | 3 |
| Headache | 0 | 1 | 2 | 3 |
| Fever / Sweating | 0 | 1 | 2 | 3 |
| Please mark on the line in how far you are able to perform your usual daily activities | 0 - totally capable                                                  10 - totally incapable | | | |

Figure 1

TREATMENT OF MODERATE TO SEVERE INFLUENZA

CROSS REFERENCE TO RELATED APPLICATIONS

This application is a United States Application under 35 U.S.C. 371 claiming benefit of PCT Application No. PCT/EP2016/082307, filed on Dec. 22, 2016, which claims the benefit of European Application No. 15202212.5, filed on Dec. 22, 2015, the contents of each of which are incorporated herein by reference.

FIELD

The present invention relates to inhalative compositions for use in the treatment of moderate to severe influenza.

BACKGROUND

Influenza, sometimes referred to as 'the flu', is a highly contagious and acute viral infection of the respiratory tract caused by a group of RNA viruses from the Orthomyxoviridae family, namely influenza viruses A, B, and C. The first two types are responsible for the annual epidemic and pandemic outbreaks of the disease. Type C causes milder infections that do not cause epidemics and have not such a severe public health impact as types A and B. Influenza is typically characterised by a sudden onset of distinctive malaise (feeling unwell), fatigue, cough (usually dry), headache, muscle and joint pain, and most often fever, as well as inflammations of the respiratory tract mucous membranes, noticeable as sore throat and/or runny nose.

Mild forms of influenza—i.e. acute but uncomplicated—usually last a few days only, do not require hospitalisation of the patient (so-called outpatient illness) and are often self-limiting such that most people recover by themselves from a bout of influenza. However, there are also more severe forms which are characterised by a higher level of intensity in most or all symptoms and which may cause complications, sometimes fatal, such as viral pneumonia or secondary bacterial infections. Severe influenza and complications due to infection, including hospitalization and death, may occur in elderly persons, in very young persons, in persons with underlying medical conditions (including pulmonary and cardiac disease, diabetes mellitus, and immunosuppression), but also in previously healthy persons. And there continues to be a large number of people who require hospital treatment and/or die from the disease every year: worldwide, these annual epidemics result in about three to five million cases of severe illness, and about 250000 to 500000 deaths according to WHO-reports. Furthermore, influenza accounts for around 10% of sickness absence from work in Europe. Also a number of primary medical conditions such as diabetes, COPD or other chronic lung diseases may be worsened when the patient is additionally suffering from an influenza infection, often requiring hospital treatment as well. Hence, influenza presents serious public health and economic problems.

Although epidemics of influenza occur almost every year in temperate climates, the rate and severity of illness caused can vary substantially from year to year. The severity of annual epidemics is affected by several factors including the types, subtypes and strains of circulating (for instance, avian flu is frequently more severe, since there is little natural immunity in humans) and/or the level of protective antibodies in the affected population (e.g. lower levels may be present in young and elderly populations or patients with impaired immune system function).

Despite significant research efforts in the last decades, there are only few drugs against influenza viruses available, e.g. adamantane derivatives like amantadine and rimantadine (inhibiting replication of influenza type A viruses, but not B); and neuraminidase inhibitors such as the orally administered oseltamivir and the inhalative zanamivir (blocking neuraminidase, a viral enzyme common in both influenza A and B viruses). All of these drugs are directed against the virus as such. The problem with this approach is that resistances can develop relatively quickly. For instance, in May-September 2011 a widespread cluster of resistant H1N1-viruses was reported in Australia and there is great fear about even wider circulation of multi-drug resistant influenza strains. In addition to the problems of resistance, current therapies are limited in their ability to modify the course of disease when started after 48 h of illness. Furthermore, the standard therapy with oseltamivir is not sufficiently efficacious in severely affected, hospitalized patients. Thus there is an urgent need for new and effective anti-influenza drugs, especially for antivirals with novel mechanisms of action.

For instance, one approach in prior art was to not target the virus but its host cells instead, since due to the usually very small genomes of viruses and the limited coding capacity associated therewith, all viruses rely to a large extent on functions of their host cells for most of the functions necessary for their replication. By influencing such cellular functions of the host cell, it is possible to negatively affect viral replication, while there is no possibility of virus adaption (e.g. in particular by mutation) to replace the missing cellular function. This concept has already been tested on influenza A viruses using relatively unspecific inhibiting substances against cellular kinases and methyl transferases (Scholtissek and Müller, Arch. Virol. 119, 111-118, 1991).

WO 2009/089822 A2 as well as WO 2004/060360 A1 describe the use of acetylsalicylic acid (ASA) or its salt derivative D,L-lysine acetylsalicylate.glycine (LASAG) in the prophylaxis and/or treatment of viral diseases such as influenza. ASA is said to inhibit the transcription factor NF-κB in host cells, leading to essential viral components remaining in the host cell nucleus with the effect that they cannot be incorporated into viral particles anymore such that virus replication is inhibited. WO 2004/060360 A1 further describes a pharmaceutical composition formulated for bronchial administration by way of an aerosol and proposes a daily ASA dose for humans in the range of 0.1 to 70 mg, as derived from animal studies. WO 2009/089822 A2 tests doses of up to 350 mg LASAG (corresponding to 175 mg ASA) administered in a single inhalation to a small set of four humans suffering from unspecified bronchial infections.

However, the prior art documents are silent on the treatment of in particular more severe forms of influenza, or on the treatment of primary medical conditions which are worsened by influenza infections, or on improvements of the current standard influenza treatments, aimed to overcome the above mentioned drawbacks. It is thus an object of the present invention to provide a compound and/or a composition for use in the treatment of influenza, in particular of moderate to severe influenza. Further objects will become apparent on the basis of the following description including the examples, and the patent claims.

SUMMARY OF THE INVENTION

In a first aspect, the invention provides acetylsalicylic acid (ASA) or a pharmaceutically acceptable salt thereof, or a pharmaceutical composition comprising ASA or a pharmaceutically acceptable salt thereof, for use in the treatment of a patient (e.g. a human) suffering from a moderate to severe influenza virus infection and/or a symptom or condition associated therewith (namely symptoms or conditions such as nasal congestion, sore throat, cough, fever, fatigue, headache and myalgias), wherein said use comprises the administration of a composition comprising ASA or a pharmaceutically acceptable salt thereof to the patient by inhalation at a daily dose of ASA of at least about 600 mg, for instance at a daily dose of ASA from about 600 mg to about 2000 mg, or from about 960 mg to about 1440 mg, or from about 1080 mg to 1320 mg, or about 1200 mg. In one aspect, the influenza may be caused by an influenza A virus or an influenza B virus.

The administration of the daily dose may comprise the administration of up to four single doses at a dosing interval of at least 4 hours. Further, a total of at least 9 single doses may be administered over a treatment course of at least 3 days, using a single dose of about 400 mg ASA; e.g. 15 singles doses over a treatment course of 5 to 6 days.

The composition is administered by inhalation; for instance in the form of an aqueous solution by using a jet nebuliser or a vibrating mesh nebuliser. In order to allow for a good solubility, the ASA may be provided in the form of its D,L-lysine acetylsalicylate.glycine salt (LASAG). For instance, the composition may be provided in the form of a powder for reconstitution, which prior to inhalation may be dissolved to form an aqueous solution with a LASAG concentration of 100 mg/mL to 400 mg/mL, or with an ASA concentration of about 50 mg/mL to about 200 mg/mL. A single dose of the aqueous solution may e.g. have a volume of about 3 mL to about 5 mL, preferably 4 mL, a LASAG concentration of about 200 mg/mL, and an ASA concentration of about 100 mg/mL.

The jet nebuliser or the vibrating mesh nebuliser may be adapted to deliver the aqueous solution at a controlled inspiratory flow and/or a controlled inspiratory volume; e.g. a controlled inspiratory flow of about 200 mL/sec and/or a controlled inspiratory volume of about 800 mL. This typically allows a single dose to be administered over the course of about 90 to about 105 breaths within an administration time of about 12 to about 14 minutes.

In one aspect of the invention, the patient may be human and may be hospitalized due to the influenza virus infection and/or a symptom or condition associated therewith (e.g. nasal congestion, sore throat, cough, fever, fatigue, headache and myalgias).

OVERVIEW OF FIGURES

FIG. 1: Patient questionnaire on the 7 clinical influenza symptoms to evaluate a composite symptom score (CSS) according to the invention at baseline and during treatment FIG. 2: Kaplan-Meier estimation plot of survival distribution function over time to alleviation T1 for placebo versus LASAG treatment for patients having moderate or severe influenza (CSS≥14)

Figure 3:
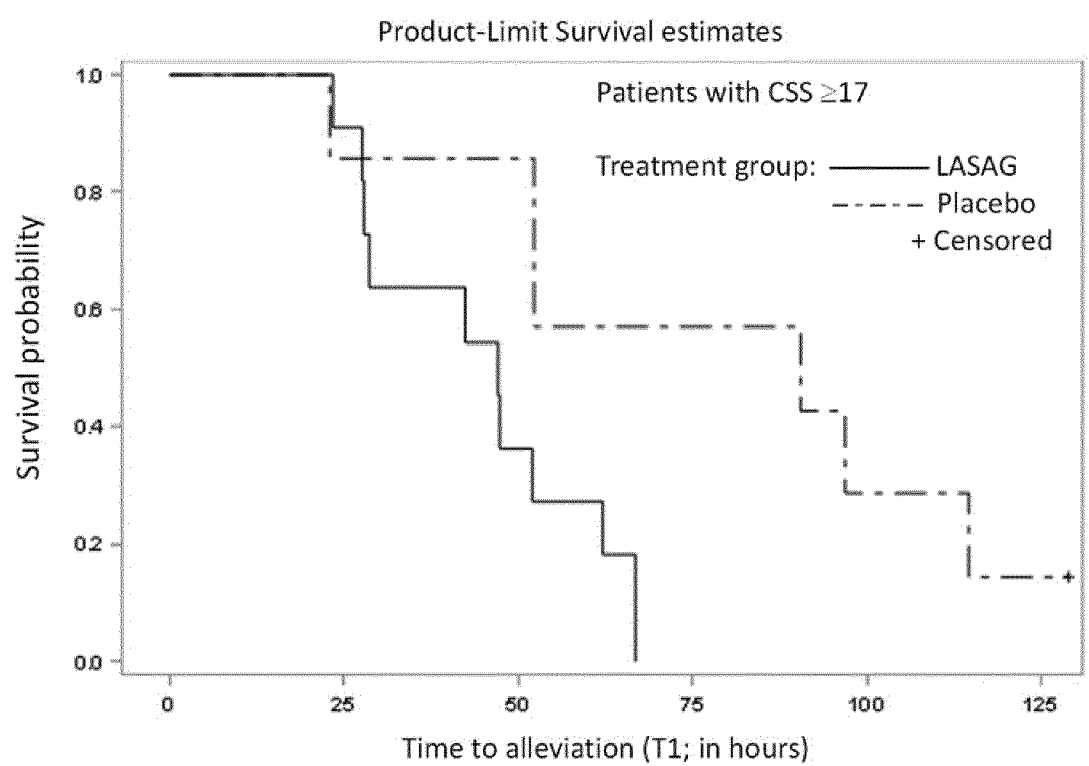

FIG. 3: Kaplan-Meier estimation plot of survival distribution function over time to alleviation T1 for placebo versus LASAG treatment for patients having severe influenza (CSS≥17)

Figure 4:
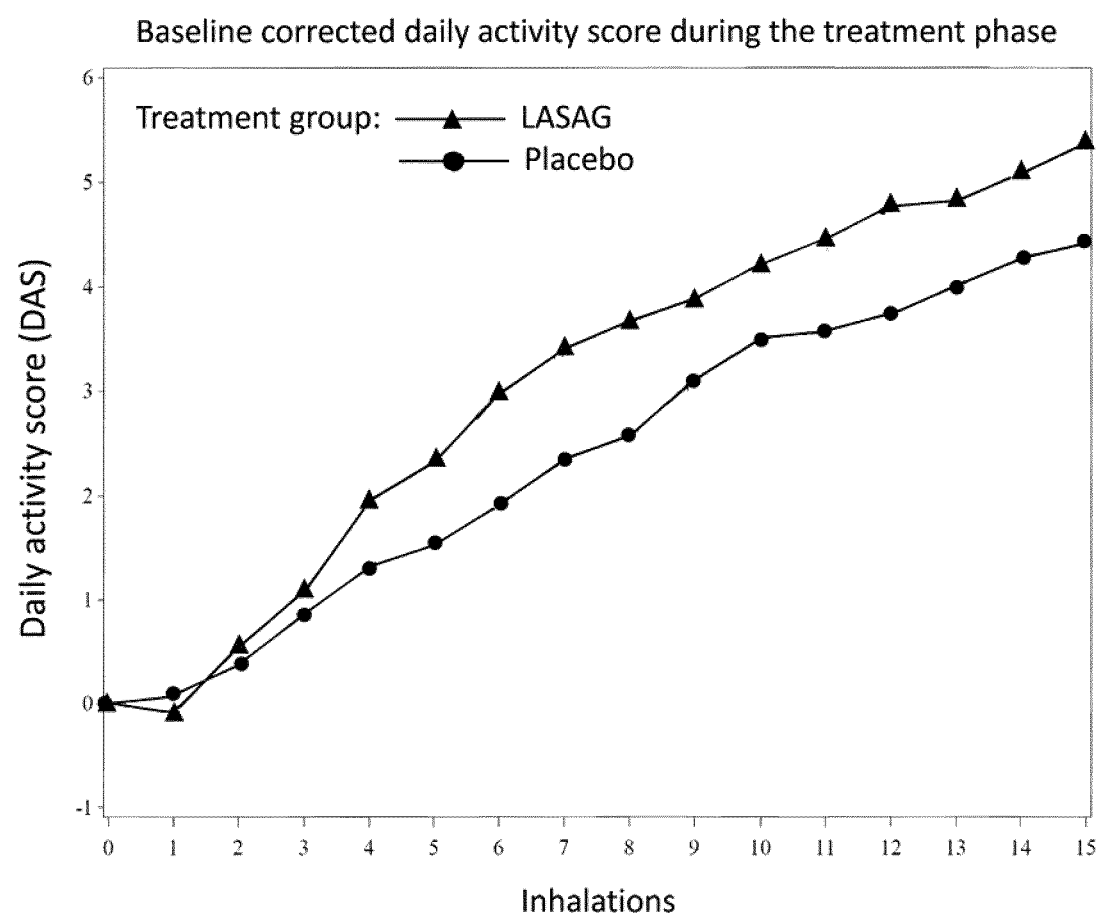

FIG. 4: Baseline corrected daily activity scores (DAS) curves of the LASAG group and the placebo group over the number of inhalations.

DETAILED DESCRIPTION OF THE INVENTION

In a first aspect, the invention provides acetylsalicylic acid (ASA) or a pharmaceutically acceptable salt thereof for use in the treatment of a patient suffering from a moderate to severe influenza virus infection and/or a symptom or condition associated therewith, wherein the use comprises the administration of a composition comprising ASA or a pharmaceutically acceptable salt thereof to the patient by inhalation at a daily dose of ASA of at least about 600 mg. According to this aspect, a novel use of acetylsalicylic acid (ASA) or a pharmaceutically acceptable salt thereof is provided, which is the use of the compound for the treatment of a patient suffering from a moderate to severe influenza virus infection and/or a symptom or condition associated therewith, comprising the administration of a composition comprising ASA or a pharmaceutically acceptable salt thereof to the patient by inhalation at a daily dose of ASA of at least about 600 mg. The novel use may also be expressed as the use of acetylsalicylic acid (ASA) or a pharmaceutically acceptable salt thereof for the manufacture of a medicament for the treatment of a patient suffering from a moderate to severe influenza virus infection and/or a symptom or condition associated therewith by administering a composition comprising ASA or a pharmaceutically acceptable salt thereof to the patient by inhalation at a daily dose of ASA of at least about 600 mg. The novel use may also be expressed as a method for the treatment of a patient suffering from a moderate to severe influenza virus infection and/or a symptom or condition associated therewith comprising a step of administering acetylsalicylic acid (ASA) or a pharmaceutically acceptable salt thereof, wherein a composition comprising ASA or a pharmaceutically acceptable salt thereof is administered to the patient by inhalation at a daily dose of ASA of at least about 600 mg. Symptoms or conditions associated with a moderate to severe influenza virus infection include, for instance, nasal congestion, sore throat, cough, fever, fatigue, headache and myalgias.

An example of a pharmaceutically acceptable salt form of ASA is the lysine salt of the compound, optionally in combination with glycine (LASAG).

In a further aspect, the invention provides a pharmaceutical composition comprising acetylsalicylic acid (ASA) or a pharmaceutically acceptable salt thereof for use in the treatment of a patient suffering from a moderate to severe influenza virus infection and/or a symptom or condition associated therewith, wherein the use comprises the administration of the composition by inhalation at a daily dose of ASA of at least about 600 mg. According to this aspect, a novel use of a composition comprising acetylsalicylic acid (ASA) or a pharmaceutically acceptable salt thereof is provided, which is the use of the composition for the treatment of a patient suffering from a moderate to severe influenza virus infection and/or a symptom or condition associated therewith, comprising the administration of the composition to the patient by inhalation at a daily dose of ASA of at least about 600 mg. The novel use may also be expressed as the use of such composition for the manufacture of a medicament for the treatment of a patient suffering from a moderate to severe influenza virus infection and/or a symptom or condition associated therewith by administering the composition to the patient by inhalation at a daily dose of ASA of at least about 600 mg. The novel use may also be expressed as a method for the treatment of a patient suffering from a moderate to severe influenza virus infection and/or a symptom or condition associated therewith comprising a step of administering a composition comprising acetylsalicylic acid (ASA) to the patient by inhalation at a daily dose of ASA of at least about 600 mg.

In one aspect, the daily dose of ASA is from about 600 mg to about 2000 mg, or from about 960 mg to about 1440 mg or from about 1080 mg to 1320 mg. For instance, the daily dose may be about 1100 mg, 1150 mg, 1200 mg, 1250 mg, 1300 mg; in particular about 1200 mg.

As used herein, the term 'dose' refers to the nominally administered dose unless specified otherwise; for instance, the amount of drug as contained in a specific single dose unit which is loaded or filled into an inhalation device in order to be administered to the patient, without taking into account the inherent losses during administration (such as losses in the device, losses on exhalation or similar). In particular, specific dose fractions, such as lung dose or alveolar dose (i.e. deposition in the lungs and deposition in the alveoli) are only part of the administered dose.

In one specific embodiment, the patient suffering from a moderate to severe influenza virus infection and/or a symptom or condition associated therewith is human. Considering the currently assumed mechanism of action, though— namely, the inhibition of the transcription factor NF-κB in host cells by ASA, thereby inhibiting virus replication— there is no doubt that the treatment would be equally successful in other patient groups, too, e.g. mammals and/or productive livestock, as long the virus requires said transcription factor in host cells for its replication.

In a further specific embodiment, the human patient is hospitalized due to the influenza virus infection and/or a symptom or condition associated therewith. Hospitalisation is most commonly required for patients suffering from a moderate to severe influenza virus infection, since moderate to severe influenza is commonly characterized by a higher intensity level of most, if not all, symptoms, very often with fevers 38° C. (measured orally) even in adults and a distinct feeling of malaise which usually renders the patient unable to perform his/her routine daily activities.

Naturally the boundaries between mild forms of influenza and the more intense forms, moderate to severe influenza, are fluent and they may shift depending on the specific patient and his/her personal experience.

As used herein, moderate and severe influenza forms are defined by the so-called composite symptom score (CSS), which is calculated based on seven common influenza symptoms and a patient's rating for each of them in an influenza symptom questionnaire (as depicted in FIG. 1). The clinical influenza symptoms used for the calculation are nasal congestion, sore throat, cough, aches/myalgia (pain in limbs and/or muscles), fatigue/exhaustion, headaches as well as feverishness/chills/sweats. These are rated on a 4-point scale ranging from 0=not present, like before the influenza via 1=mild and 2=moderate to 3=severe. The seven ratings are summed up to provide a composite symptom score (CSS; maximum value of 21); at baseline in order to define the severity of the infection, and also during treatment, prior to each single dose administration in order to follow the progress of symptom alleviation. In principle, the higher the CSS value the more severe the infection. Baseline CSS values of 14 or higher and below 17 are considered moderate forms of influenza, while baseline CSS values of 17 or higher are considered to be severe forms of influenza. Baseline CSS values below 14 are considered milder forms of influenza.

Patients are considered symptom-free, or cured, if at least 5 of the 7 clinical influenza symptoms above are rated 0 or 1 on the influenza symptom questionnaire without the use of relief medications such as pain killers, and remain so for at least 24±2 hours.

It was surprisingly found by the inventors, that—despite the common concern that such doses would be poorly tolerable—the high doses administered via inhalation in a controlled clinical study were capable of treating patients suffering from moderate or severe influenza, e.g. reducing the alleviation times of clinical influenza symptoms in a patient group receiving ASA in the form of LASAG (nasal congestion; sore throat; cough; aches/myalgia; fatigue; headaches and feverishness/chills/sweating) in comparison with the placebo (0.9% saline solution), without noteworthy adverse effects.

Also surprising and entirely unexpected was the finding that these specific patient groups, i.e. patients suffering from moderate or severe symptoms as defined herein, could be effectively treated with inhaled ASA at the specified dosing regimen and responded so well, such as to experience substantially accelerated symptom alleviation in the LASAG group compared to the placebo group.

This is in particular surprising considering the finding that for patients with other forms of influenza, exhibiting a composite symptom score (CSS) below 14, no significant difference was observed between the LASAG and the placebo group in terms of the time required for alleviation of the clinical influenza symptoms; for instance, patients with a CSS below 14 which were hospitalized predominantly due to a primary medical condition like diabetes, COPD or other chronic lung disease that was worsened by the influenza infection.

The finding that in particular those patients suffering from moderate to severe influenza (CSS≥14 and <17 or CSS≥17) benefit from the inhalative use of acetylsalicylic acid (ASA) or a pharmaceutically acceptable salt thereof is in contrast to the common expectation that a specific therapy will usually provide relieve for a disease up to a certain level and then may fail to do so where the intensity of the disease increases further, yet usually not vice versa.

In one embodiment, the administration of the daily dose comprises administration of up to four single doses at a dosing interval of at least 4 hours; e.g. 4 single doses every 5 h and a sleep period of 9 h, or 3 single doses every 7 h and a sleep period of 10 h. In other words, the use of the composition according to the invention comprises the administration of the daily dose in the form of up to four single doses at a dosing interval of at least 4 hours.

In a further embodiment, a total of at least 9 single doses are administered over a treatment course of at least 3 days. In a yet further embodiment, a total of at least 9 single doses are administered over a treatment course of at least 3 days, and a single dose is about 400 mg ASA. In other words, the use of the composition according to the invention comprises the administration of a total of at least 9 single doses over a treatment course of at least 3 days, and a single dose is 400 mg ASA. For instance, a total of 15 single doses may be administered over a treatment course of 5 days, typically providing a morning inhalation, a mid-day- and an evening inhalation. Where treatment starts on day 1 with a mid-day- or evening inhalation (e.g. because the patient went to see the physician in the morning or during the day prior to beginning treatment), the 15 single doses may also be administered over a treatment course of 6 days, such that any morning- and mid-day inhalations missed on day 1 are administered on day 6 instead, in order to complete the treatment with 15 single doses.

It should be noted that while treatments with at least 9 single doses administered over a course of at least 3 days are preferred in order to ensure quickest possible and complete recovery of the patient, this is not to be misinterpreted in such a way that other, shorter schedules employing inhalative daily doses of ASA of at least 600 mg in the treatment of moderate to severe influenza would not be falling under the scope of the invention. As the specific case with a patient may be, e.g. seven inhalations, five inhalations or even single inhalations may already be successful and/or provide clinically relevant benefits for the patient suffering from moderate to severe influenza.

As mentioned above, the ASA may be provided in the form of a pharmaceutically acceptable salt thereof. In a preferred embodiment, the composition for the use according to the invention provides the acetylsalicylic acid (ASA) in the form of its D,L-lysine acetylsalicylate.glycine salt (LASAG):

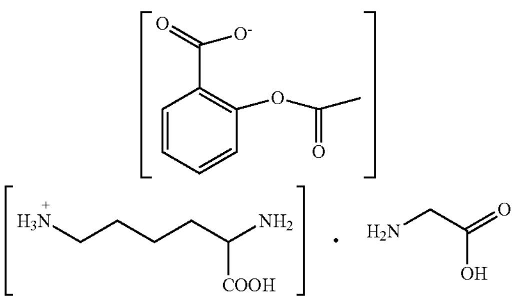

LASAG is a white powder that dissociates readily into ASA and the two amino acids lysine and glycine upon dissolution into aqueous media, resulting in a colourless and odourless solution of pH 5.9. The benefit of employing LASAG rather than ASA as such in the use according to the invention is the improved solubility of the salt in comparison with ASA (LASAG solubility about 40% or higher; see e.g. U.S. Pat. No. 4,265,888 A). Optionally, a grade of LASAG is used which comprises about 50 wt.-% of ASA, such as Aspirin® i.v.

In a specific embodiment, the LASAG composition may be provided in the form of a powder for reconstitution; i.e. a powder intended to be reconstituted with/dissolved in an aqueous medium, such as water for injection, saline or aqueous buffers. In a further specific embodiment, this LASAG composition may be provided in the form of a powder for reconstitution into an aqueous solution with a LASAG concentration of 100 mg/mL to 400 mg/mL, or with an ASA concentration of about 50 mg/mL to about 200 mg/mL; i.e. LASAG concentrations in the reconstituted solution may for instance be about 100 mg/mL, 150 mg/mL, 200 mg/mL, 250 mg/mL, 300 mg/mL, 350 mg/mL or 400 mg/mL, in particular 200 mg/mL; which may correspond to ASA concentrations in the reconstituted solution of about 50 mg/mL, 75 mg/mL, 100 mg/mL, 125 mg/mL, 150 mg/mL, 175 mg/mL or 200 mg/mL, in particular 100 mg/mL.

An exemplary LASAG composition which is commercially available and suitable for the use according to the invention is Aspirin® i.v. (formerly Aspisol®), comprising LASAG at a concentration of 200 mg/mL after correct reconstitution, equaling an ASA concentration of 100 mg/mL. At these concentrations, i.e. when employing solutions which comprise LASAG at a concentration of 200 mg/mL and ASA at a concentration of 100 mg/mL, an exemplary single administered dose of the aqueous solution may have a volume, or filled dose, of about 3 mL to about 5 mL, preferably 4 mL. This filled volume or dose is the amount that is filled into a nebuliser prior to an inhalation treatment.

It should be understood that in cases where the LASAG salt is used (rather than ASA as such), the doses and/or concentrations with respect to ASA are theoretical values based on e.g. the assumption of complete dissociation of the LASAG and calculated based on the specific ratios of lysine, glycine and ASA in the LASAG.

In one embodiment, the composition for use according to the invention—and in particular aqueous solutions of ASA or preferably LASAG as described above—is administered using a nebuliser, i.e. a drug delivery device commonly used to administer liquid compositions to a patient's respiratory system in the form of an inhalable mist of droplets. In a specific embodiment, a jet nebuliser or a vibrating mesh nebuliser is used. In other words, the use of the composition according to the invention comprises the administration of the composition using a jet nebuliser, soft mist inhaler or a vibrating mesh nebuliser. Alternatively, another type of nebuliser, such as an ultrasonic nebuliser or a soft mist inhaler, may also be used. In a further embodiment, the jet nebuliser or the vibrating mesh nebuliser is adapted to deliver the aqueous solution at a controlled inspiratory flow and/or a controlled inspiratory volume.

The inspiratory flow (or inspiratory flow rate) may range from about 150 mL/sec to about 300 mL/sec; e.g. 150 mL/sec, 200 mL/sec, 250 mL/sec or 300 mL/sec, in particular 200 mL/sec. These relatively slow flow rates are advisable due to decreased impaction drug deposition in the oropharyngeal region, which can decrease undesirable side effects.

The inspiratory volume may range from 500 mL to 1500 mL; e.g. 500 mL, 600 mL, 700 mL, 800 mL, 900 mL, 1000 mL, 1100 mL, 1200 mL, 1300 mL, 1400 mL or 1500 mL, in particular 800 mL. Larger inspiratory volumes in combination with slow inspiratory flow rates typically favour alveolar deposition and are thus preferred; yet, the volume shall be selected such that it is tolerable and can be inhaled comfortably even by patients suffering from moderate to severe influenza, who are often affected by severe coughing. In a preferred embodiment, the inspiratory volume ranges from 700 mL to 1000 mL, e.g. 800 mL. Of course, depending on the size and the physical condition of the patient, smaller volumes may also be used.

In one specific embodiment, the jet nebuliser or the vibrating mesh nebuliser is adapted to deliver the aqueous solution at a controlled inspiratory flow of about 200 mL/sec and/or a controlled inspiratory volume of about 800 mL. These settings may e.g. be achieved using the AKITA® JET nebuliser or the AKITA® Apixneb® nebuliser and setting the inhalation time to 4 seconds and the inspiratory volume to 800 mL; the devices will then guide and support the patient to perform controlled, optimized inhalation manoeuvres. Using this flow- and/or volume controlled inhalation approach, the ASA and/or or its pharmaceutically acceptable salt, such as LASAG, is selectively targeted to pre-defined target lung regions such as the alveoli of the lungs.

Using settings with an inspiratory flow of 200 mL/sec and an inspiratory volume of 800 mL, it is possible to deliver a single dose to the patient over the course of about 90 to about 105 breaths within an administration time of about 12 to about 14 minutes, e.g. in about 13 minutes.

In one specific embodiment, patients inhale about 4 mL of an aqueous solution comprising LASAG at a concentration of about 200 mg/mL (corresponding to an ASA concentration of 100 mg/mL) in nebulised form over the course of 96 breaths in order to achieve the administered single dose of about 400 mg ASA. This number of breaths may be set as a fixed value at the AKITA® devices and also displayed and/or "counted down" for the patient during the administration of a single dose, along with a fixed inspiratory phase and expiratory phase of 4 seconds each, such that these 96 breaths result in a duration of about 12.8 minutes for the administration of a single dose of 400 mg ASA (4 mL of 100 mg/mL ASA), unless where the patient requires pauses during the inhalation treatment.

With regard to dosing and deposition in the lungs and/or the alveoli in particular, it should be noted that these deposition fractions may vary with e.g. the type of drug (ASA, LASAG or other ASA derivatives, such as other pharmaceutically acceptable salts of ASA) and/or the concentration of the drug solution. Thus, when working e.g. with a drug solution of a different concentration and/or a different ASA derivative, the specific nebulisation behaviour of the ASA formulation in question may change so that the administered dose may have to be re-calculated and adjusted accordingly.

In one specific aspect of the invention, the influenza infection is caused by an influenza A virus or an influenza B virus.

Apart from treating the influenza infection as such, the inhalative ASA administrations according to the invention—optionally using ASA in the form of ASA derivatives such as pharmaceutically acceptable salts like LASAG—may also be used for the purpose of treating patients suffering from a symptom or condition associated with the influenza virus infection, namely a symptom or condition which may be selected from nasal congestion, sore throat, cough, fever, fatigue, headache and myalgias. For instance, the inhalative ASA administration according to the invention may be used to treat severe influenza-induced coughing, e.g. where this cough is not or not sufficiently controlled by other cough suppressants. Alternatively, the inhalative ASA administration according to the invention may be used to treat the influenza-induced fatigue, fever and/or myalgias.

In another aspect, the inhalative ASA administrations according to the invention may also be used in treating patients who suffer from a moderate or severe form of influenza (CSS≥14 and <17 or CSS≥17) and one or more other primary medical diseases or conditions which are worsened/exacerbated by an influenza infection. Examples of such diseases or conditions include but are not limited to diabetes, COPD and other chronic lung diseases. Irrespective of the presence of a primary medical disease or condition, all patients included in the study showing a moderate to severe form of influenza (CSS≥14 and <17 or CSS≥17) were treated successfully by administration of a composition comprising ASA or a pharmaceutically acceptable salt thereof to the patients by inhalation at a daily dose of ASA of at least 600 mg; e.g. resulting in significantly shorter times of alleviation of clinical influenza symptoms in the LASAG group compared to the placebo group.

EXAMPLES

Example 1: Clinical Safety

In a controlled clinical environment, 38 healthy adults received single doses of either 0.9% saline solution as placebo or up to 750 mg of ASA by inhalation (placebo n=10, ASA n=28). ASA was administered in the form of an aqueous liquid solution comprising LASAG at a concentration of about 200 mg/ml, corresponding to an ASA concentration of about 100 mg/ml, using the AKITA® Apixneb® device at controlled inspiratory flow rate of 250 mL/sec and controlled volume of 800 mL.

In result, the administered doses were overall well tolerated; no serious events or severe adverse effects were observed and none of the participating subjects discontinued the study. The most frequently occurring treatment-emergent adverse effects were drug-related throat irritation and productive cough as well as vessel puncture site reactions from the diagnostic procedures. Although a higher rate of throat irritation occurred at higher doses, no effect on pulmonary function tests parameters was seen. The maximum intensity of most adverse effects was rated as 'mild'; with only 2 subjects reporting 'moderate' adverse effects and no 'severe' adverse effects. In addition, all treatment emergent adverse effects were 'resolved/recovered' at the end of the study.

Example 2: Clinical Phase II Study on Safety and Efficacy of Inhaled LASAG and Placebo in Adult Hospitalized Patients with Moderate to Severe Influenza In a multi-centre, randomised, double-blind, placebo controlled study with about 110 enrolled patients, inhaled LASAG was evaluated versus inhalation of placebo in adult patients who were hospitalized due to moderate to severe influenza and/or an influenza caused worsening of a another primary medical condition (e.g. diabetes, COPD, or other chronic lung diseases). Of these 110 enrolled patients, 81 were confirmed by a reverse transcription polymerase chain reaction (RT-PCR) test to be infected with an influenza virus, and received at least one inhalation of LASAG or placebo. It should be noted that although ASA is the active compound as explained above, the term LASAG inhalation or LASAG group is used throughout this study described below.

Patients, aged 18-80 years, who reported the onset of illness less than 120 hours (ideally less than 72 hours) before the first study drug application, who showed at least one respiratory symptom (nasal congestion, sore throat or cough) as well as at least one constitutional symptom (aches/myalgia, fatigue, headache or feverishness/chills/sweat) and who further had fever of ≥38.0° C. (orally) or ≥38.5° C. (rectally or tympanic) at time of screening or any time during the 48 hours prior to screening, were enrolled in the study. Influenza infection was further re-confirmed by a reverse transcription polymerase chain reaction (RT-PCR) test.

Main exclusion criteria included pregnancy, allergies/hypersensitivities to LASAG or ASA, admittance to intensive care unit (ICU) due to breathing instability, inability to breathe from a nebuliser, evidence or suspicion of an acute non-influenza infectious illness as well as immunisations against influenza with live attenuated virus vaccine in the 4 weeks prior to the study.

During the study, patients received inhalations three times daily of either:
a) a 4 mL fill dose comprising 800 mg LASAG (equivalent to 400 mg ASA), or
b) a 4 mL fill dose of placebo, namely 0.9% saline solution (0.9% NaCl).

Prior to each inhalation, the LASAG solution was freshly reconstituted (no longer than 30 minutes before usage), in order to prevent or limit the degradation of ASA in water. In the specific study described here, commercially available Aspirin® i.v. was used to prepare the LASAG solutions.

Further, prior to each inhalation, clinical data such as body temperature, oxygen saturation, breathing rate etc. were recorded by the investigators at the study centre, and an influenza symptom questionnaire (as depicted in FIG. 1) was filled in; summarizing seven clinical influenza symptoms (namely, nasal congestion; sore throat; cough; aches/myalgia; fatigue; headaches and feverishness/chills/sweats) and rating them on a 4-point scale (0=not present, like before the influenza, 1=mild, 2=moderate, 3=severe) as well as the ability to perform usual activities using a 0-10 visual analogue scale (0=unable to perform any usual activities to 10=able to perform all usual activities fully). These ratings of symptoms were summed up to provide a composite symptom score (CSS); the higher the CSS (max. 21) the more severe the disease. Baseline CSS values ≥14 and <17 were considered to be moderate forms of influenza, while baseline CSS values ≥17 were considered to be severe forms of influenza. Baseline CSS values below 14 were considered milder forms of influenza.

Using an AKITA® JET nebuliser (set for all patients to an inhalation volume of 800 mL over a set inhalatory period of 4 seconds; i.e. flow-rate of 200 mL/sec), the three inhalations were administered at 7-9 a.m. (morning), 12 a.m.-2 p.m. (mid-day) and at 5-7 p.m. (evening) and always at least 4 h apart. A total of 15 inhalations were administered over the course of 5 days (or 6 days in cases where patients started the study on the first study day with the mid-day or evening inhalation; the "missed inhalations" of day 1 were then done on day 6).

Any standard of care practised at the study centre sites for influenza patients was allowed with a few restrictions:
a) where considered necessary, paracetamol (acetaminophen) was used as symptom relief medication (e.g. pain);
b) where considered necessary, oral oseltamivir was used as antiviral therapy.

Where patients received oseltamivir as standard of care at the respective study site, this treatment was initiated prior to the first inhalation (start of the study) and continued for a minimum of 5 days (according to oseltamivir's label).

The primary objective of the study was to evaluate the clinical efficacy of inhaled LASAG plus standard of care compared to placebo plus standard of care in patients hospitalized due to acute serious influenza and/or an influenza caused worsening of a primary medical condition, measured by the time to alleviation of clinical influenza symptoms (primary variable T1). T1 was defined as the time in hours from first inhalation until at least 5 of the 7 clinical influenza symptoms (see above) are rated 0 or 1 on the influenza symptom questionnaire without the use of relief medication (acetaminophen) and remained so for at least 24±2 hours. Further, patients were considered 'completely healed' if all of the 7 clinical influenza symptoms were rated 0 or 1 on the influenza symptom questionnaire.

The secondary objectives of the study comparing inhaled LASAG plus standard of care to placebo plus standard of care in patients hospitalized due to acute serious influenza and/or an influenza caused worsening of a primary medical condition included the evaluation of:
a) clinical efficacy as determined by a routine daily activity score (DAS) ranging from 0=unable to perform one's routine daily activities at all to 10=fully able to perform one's routine daily activities (measured by a regular ruler starting from 0 to the nearest 0.1 cm and documented together with date and time),
b) safety and tolerability by documenting transient local side effects (e.g. cough, taste changes or pharyngeal irritations by LASAG-inhalation) and treatment emergent adverse events (TEAEs), especially those associated with ASA, such as bleeding, bruising, tinnitus, bronchospasm or Reye-syndrome
c) mortality at last follow-up visit (23±2 days after end of treatment).

Analysis of the obtained study data with regard to time to alleviation of clinical influenza symptoms (primary variable T1) was performed in the so-called 'per protocol' data set (PP), including all subjects with influenza infection confirmed by RT-PCR who had at least 13 of the intended 15 inhalations of LASAG or placebo and no major protocol deviations (such as un-blinding of the inhalation solution, >2 solutions administered >30 minutes after their preparation by reconstitution, ≥3 symptom questionnaires missing etc.).

Analysis of the obtained study data with regard to secondary variables such as the daily activity score (DAS) was performed in the so-called 'modified intention to treat' data set (MITT; including all subjects with influenza infection confirmed by RT-PCR who had at least one of the intended 15 inhalations of LASAG or placebo); or for the safety and tolerability analysis in the so-called 'safety set' (includes the 'MITT' patients as well as 26 further patients who also received the treatment of LASAG or placebo but had no influenza infection).

All data of the patients were used as available; cases of missing data of the primary variable (T1) and other time to event data were interpreted as censored cases (e.g. missing data at baseline will be substituted by the corresponding values at screening). Where such censoring occurred, log rank tests and Kaplan-Meier estimates were employed for statistical analysis. Results were interpreted in an exploratory way.

The 'per protocol' set included 41 patients having moderate or severe influenza (i.e. with a CSS of ≥14 at baseline), of which a total of 40 were characterized as alleviated during the observation period. Further, of these 41 patients with a CSS of ≥14 at baseline 18 were affected by severe influenza (i.e. CSS≥17), of which 17 were characterized as alleviated during the observation period; only 1 patient in the placebo group left the study without alleviation of symptoms as defined above. Thus the rates of alleviated patients were similar for both the LASAG and the placebo groups; however, the time to alleviation of clinical influenza symptoms (primary variable T1) differed between LASAG and Placebo group, as was confirmed by log rank test.

The study data analysis revealed that the time to alleviation of influenza symptoms T1 was significantly reduced in the LASAG-group compared to the placebo group; from 51.6 h to 38.3 h in patients with CSS≥14 (p-value: log rank test 0.0313) and from 71.5 h to 44.7 h in patients with CSS≥17 (p-value: log rank test 0.0152). This difference was also illustrated by the Kaplan-Meier estimation plots, in which the two curves were crossing each other until about 20-25 hours of observation. From then on the LASAG curve is lower than the placebo curve (see FIG. 2 and FIG. 3 for the patient group subsets having moderate or severe influenza (CSS≥14) and those affected by severe influenza (CSS≥17), respectively).

The results are summarised in Table 1 below:

| | | Time to alleviation of clinical influenza symptoms in hours | | | | | | |
|---|---|---|---|---|---|---|---|---|
| | | Number of patients | Mean | Median | Standard Deviation | Min. | Max. | Q1 | Q3 |
| CSS ≥ 14 | LASAG | 24 | 38.3 | 27.8 | 18.0 | 9.8 | 67.4 | 23.5 | 52.4 |
| | Placebo | 16 | 51.6 | 47.0 | 31.9 | 3.4 | 114.5 | 23.8 | 78.4 |
| CSS ≥ 17 | LASAG | 11 | 44.7 | 47.0 | 16.2 | 23.5 | 66.9 | 27.8 | 62.1 |
| | Placebo | 6 | 71.5 | 71.3 | 34.5 | 23.0 | 114.5 | 52.2 | 96.8 |

Assuming that patients started with the morning inhalation, the results may also be interpreted in such a way that patients with CSS≥17 were alleviated after about 9 placebo inhalations versus only about 6 LASAG inhalations.

With regard to the secondary objectives the study data analysis further revealed that the LASAG group showed a better recovery than the placebo group over the full range of inhalation times after inhalation 1, as can be seen in FIG. 4 depicting the baseline corrected daily activity scores (DAS) curves of the LASAG group and the placebo group over the number of inhalations.

With regard to the secondary objective to evaluate safety and tolerability the study data analysis further revealed that a total of 83 adverse events (AE) were reported, affecting 44 patients (of the total 107 patients in the 'safety set'): 41 AE (=49.4%) in the LASAG group and 42 (=50.6%) in the placebo group. The number of affected patients is 23 (41.1%) in the LASAG group patients and 21 (41.2%) in the placebo group patients. This means that there were no significant differences between placebo and LASAG groups with regard to tolerability (Chi square test: p=0.9912). Common AEs mainly included gastro-intestinal effects such as diarrhea, constipation or vomiting; or respiratory effects such as throat irritations or coughing.

The majority of these AEs (>73%) were graded as 'mild', some as 'moderate'; The only 'severe' graded AE, a respiratory nosocomial infection, occurred in the placebo group. About 56.1% of the LASAG group required medication due to AEs compared to 55.4% of the placebo group; thus, again no major differences between placebo and LASAG groups. All treatment emerging adverse events were resolved at the end of the study. There was no case of death or other significant adverse events.

The invention claimed is:

1. A method for treating of a patient suffering from a moderate to severe influenza virus infection and/or a symptom or condition associated therewith, the method comprising administration of a composition comprising acetylsalicylic acid (ASA) or a pharmaceutically acceptable salt thereof to the patient by inhalation at a daily dose of ASA of at least 600 mg, wherein the patient suffering from moderate to severe influenza exhibits a baseline composite symptom score (CSS) values of 14 or higher.

2. A method according to claim 1, wherein the daily dose of ASA is from 960 mg to 1440 mg, or from 1080 mg to 1320 mg, or 1200 mg.

3. A method according to claim 1, wherein the administration of the daily dose comprises administration of up to four single doses at a dosing interval of at least 4 hours.

4. A method according to claim 1, wherein a total of at least 9 single doses are administered over a treatment course of at least 3 days, and wherein a single dose is 400 mg ASA.

5. A method according to claim 1, wherein the ASA is provided in the form of its D,L-lysine acetylsalicylate glycine salt (LASAG).

6. A method according to claim 5, wherein the composition is provided in the form of a powder for reconstitution into an aqueous solution with a LASAG concentration of 100 mg/mL to 400 mg/mL, or with an ASA concentration of 50 mg/mL to 200 mg/mL.

7. A method according to claim 6, wherein a single dose of the aqueous solution has a volume of 3 mL to 5 mL, a LASAG concentration of 200 mg/mL, and an ASA concentration of 100 mg/mL.

8. A method according to claim 6, wherein the composition is administered using a jet nebuliser or a vibrating mesh nebuliser.

9. A method according to claim 8, wherein the jet nebuliser or the vibrating mesh nebuliser is adapted to deliver the aqueous solution at a controlled inspiratory flow and/or a controlled inspiratory volume.

10. A method according to claim 9, wherein the inspiratory flow is 200 mL/sec and/or the inspiratory volume is 800 mL.

11. A method according to claim 8, wherein the jet nebuliser or the vibrating mesh nebuliser is adapted to deliver a single dose over the course of 90 to 105 breaths within an administration time of 12 to 14 minutes.

12. A method according to claim 1, wherein the patient is hospitalized due to the influenza virus infection and/or a symptom or condition associated therewith.

13. A method according to claim 1, wherein the influenza infection is caused by an influenza A virus or an influenza B virus.

14. A method according to claim 1, wherein the symptom or condition associated with the influenza virus infection is selected from nasal congestion, sore throat, cough, fever, fatigue, headache and myalgias.

15. A method according to claim 1, wherein the composition is administered using a jet nebuliser or a vibrating mesh nebuliser.

* * * * *